United States Patent [19]

Buynak et al.

[11] Patent Number: 5,681,563
[45] Date of Patent: Oct. 28, 1997

[54] 7-VINYLIDENE CEPHALOSPORINS AND METHODS OF USING THE SAME

[75] Inventors: John D. Buynak; Brian Bachmann, both of Dallas, Tex.

[73] Assignee: Research Corporation Technologies, Inc., Tucson, Ariz.

[21] Appl. No.: 664,493

[22] Filed: Jun. 17, 1996

Related U.S. Application Data

[62] Division of Ser. No. 354,858, Dec. 9, 1994, Pat. No. 5,597,817.

[51] Int. Cl.[6] .............. A61K 35/66; A61K 31/545; A61K 31/43
[52] U.S. Cl. .............. 424/114; 514/200; 514/201; 514/208; 514/209; 514/197; 514/196
[58] Field of Search .............. 424/114; 514/200, 514/201, 208, 209, 196, 197

[56] References Cited

U.S. PATENT DOCUMENTS

| | | | |
|---|---|---|---|
| 4,150,156 | 4/1979 | Beattie et al. | 424/246 |
| 4,992,541 | 2/1991 | Blacklock et al. | 540/221 |
| 5,077,286 | 12/1991 | Bissolino et al. | 514/201 |
| 5,126,446 | 6/1992 | Brown, Jr. et al. | 540/230 |
| 5,258,377 | 11/1993 | Maiti et al. | 540/221 |
| 5,264,429 | 11/1993 | Maiti et al. | 514/202 |
| 5,364,848 | 11/1994 | Doherty et al. | 514/201 |
| 5,446,037 | 8/1995 | Maiti et al. | 514/201 |

*Primary Examiner*—Jerome D. Goldberg
*Attorney, Agent, or Firm*—Schwegman, Lundberg, Woessner & Kluth, P.A.

[57] ABSTRACT

Cephalosporins with an exocyclic allene in the 7-position and their pharmaceutically active salts are potent inhibitors of β-lactamases and are therefore useful in the treatment of penicillin resistant infections.

4 Claims, No Drawings

7-VINYLIDENE CEPHALOSPORINS AND METHODS OF USING THE SAME

This is a Division of application Ser. No. 08/354,858 filed on Dec. 9, 1994, now U.S. Pat. No. 5,597,817.

This invention was made with Government support under Contract No. 5R01-GM-37774, awarded by the National Institutes of Health. The Government has certain rights in the invention.

BACKGROUND OF THE INVENTION

1. Field of the Invention

The present invention relates to a new class of chemical compounds, specifically 7-vinylidene cephalosporins, pharmaceutically acceptable salts thereof and a method of inhibiting β-lactamases.

2. Discussion of the Background

The most important mechanism of microbial resistance to β-lactam antibiotics is the bacterial production of β-lactamases, enzymes which hydrolytically destroy β-lactam antibiotics, such as penicillins and cephalosporins. This type of resistance can be transferred horizontally by plasmids that are capable of rapidly spreading the resistance, not only to other members of the same strain, but even to other species. Due to such rapid gene transfer, a patient can become infected with different organisms, each possessing the same β-lactamase.

β-lactamase enzymes have been organized into four molecular classes: A, B, C, and D based on amino acid sequence. Class A, which includes RTEM and the β-lactamase of *Staphylococcus aureus*, class C, which includes the lactamase derived from P99 *Enterobacter cloacae*, and class D are serine hydrolases. Class A enzymes have a molecular weight of about 29 kDa and preferentially hydrolyze penicillins. The class B lactamases are metalloenzymes and have a broader substrate profile than the proteins in the other classes. Class C enzymes include the chromosomal cephalosporinases of gram-negative bacteria and have molecular weights of approximately 39 kDa. The recently recognized class D enzymes exhibit a unique substrate profile which differs significantly from both class A and class C.

The class C cephalosporinases, in particular, are responsible for the resistance of gram-negative bacteria to a variety of both traditional and newly designed antibiotics. The Enterobacter species, which possess a class C enzyme, are now the third greatest cause of hospital-acquired infections in the United States. This class of enzymes often has poor affinities for inhibitors of the class A enzymes, such as clavulanic acid, a commonly prescribed inhibitor, and to common in vitro inactivators, such as 6-β-iodopenicillanate.

One strategy for overcoming rapidly evolving bacterial resistance is the synthesis and administration of β-lactamase inhibitors. Frequently, β-lactamase inhibitors do not possess antibiotic activity themselves and are thus administered together with an antibiotic. One example of such a synergistic mixture is "augmentin", which contains the antibiotic amoxicillin and the β-lactamase inhibitor, clavulanic acid.

It is thus desirable to find novel β-lactamase inhibitors which can be coadministered with a β-lactam antibiotic.

SUMMARY OF THE INVENTION

Accordingly, one object of the present invention is to provide novel β-lactamase inhibitors.

It is another object of the present invention to provide pharmaceutical compositions useful for inhibiting a β-lactamase.

It is another object of the present invention to provide pharmaceutical compositions with increased β-lactam antibiotic activity.

It is another object of the present invention to provide methods of inhibiting a β-lactamase.

It is another object of the present invention to provide methods of enhancing the biological activity of a β-lactam antibiotic.

These and other objects, which will become apparent during the following detailed description, have been achieved by the inventors' discovery that compounds of the formula (1)

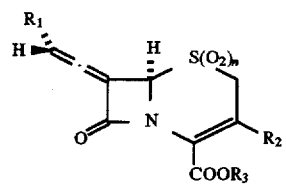

wherein n is 0 or 1 (the sulfide or the sulfone, respectively);

$R_1$ is selected from the group consisting of
  a) hydrogen;
  b) linear or branched $C_{1-10}$-alkyl;
  c) halogen;
  d) hydroxy-$C_{1-10}$-alkyl;
  e) $C_{1-10}$-alkoxy;
  f) $C_{2-10}$-alkanoyloxy;
  g) $C_{2-10}$-alkene;
  h) $C_{2-10}$-alkene substituted with one or more groups selected from the group consisting of chlorine, fluorine, bromine or phenyl;
  i) $C_{1-10}$-alkoxycarbonyl;
  j) $C_{1-10}$-alkoxycarbamido;
  k) N-$C_{1-10}$-alkoxy-N-$C_{1-10}$-alkylaminocarbonyl;
  l) halo-$C_{1-10}$-alkyl;
  m) $C_{6-10}$-aryl;
  n) $C_{6-10}$-aryl substituted with one or more groups selected from the group consisting of ethyl, n-propyl, isopropyl, amino, methylamino and dimethylamino; and,
  o) —COOH or —COOY, wherein Y is a pharmaceutically acceptable cation;

$R_2$ is selected from the group consisting of
  1) —COOH;
  2) Cl or F;
  3) trifluoromethyl;
  4) —CHO; and,
  5) —CH$_2$M, wherein M is selected from the group consisting of
    a) hydrogen;
    b) halo;
    c) hydroxy;
    d) $C_{1-10}$-alkoxy;
    e) $C_{6-10}$-aryloxy;
    f) $C_{6-10}$-aryl-$C_{1-10}$-alkoxy;
    g) mercapto;
    h) mercapto substituted with one or more groups selected from the group consisting of methyl, ethyl or phenyl;
    i) $C_{2-10}$-acylthio;
    j) $C_{2-10}$-acyloxy or carbamoyloxy;
    k) $C_{2-10}$-acyloxy or carbamoyloxy substituted with one or more groups selected from the group consisting of

3

—COOH, aminophenyl, phenyl, $C_{1-6}$-alkyl, chlorine, bromine or fluorine;
l) a quaternary ammonium salt;
m) amino or amido; and,
n) amino or amido substituted with one or more groups selected from the group consisting of $C_{1-10}$-alkyl groups;

$R_3$ is selected from the group consisting of
a) hydrogen; and,
b) pharmaceutically acceptable cations;
are effective β-lactamase inhibitors.

DETAILED DESCRIPTION OF THE PREFERRED EMBODIMENTS

Thus, in a first embodiment, the present invention provides novel compounds of the formula (1)

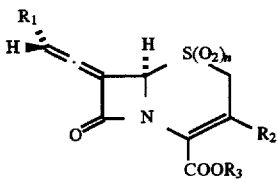

wherein n is 0 or 1;

$R_1$ is selected from the group consisting of
a) hydrogen;
b) linear or branched $C_{1-10}$-alkyl, preferably, $C_{1-6}$-alkyl, more preferably, methyl, ethyl, n-propyl, isopropyl, n-butyl, t-butyl, n-pentyl, cyclopropyl, cyclopentyl, or cyclohexyl, most preferably t-butyl;
c) halogen, preferably Br or Cl;
d) hydroxy-$C_{1-10}$-alkyl, preferably, hydroxy-$C_{1-6}$-alkyl, more preferably, hydroxymethyl, 1-hydroxyethyl or 2-hydroxyethyl;
e) $C_{1-10}$-alkoxy, preferably, $C_{1-6}$-alkoxy, more preferably, t-butoxy or methoxy;
f) $C_{2-10}$-alkanoyloxy, preferably, $C_{2-6}$-alkanoyloxy, more preferably, acetoxy or propanoyloxy;
g) $C_{2-10}$-alkene, preferably, $C_{2-6}$-alkene, more preferably, ethylene, 1-propylene or 2-propylene;
h) substituted $C_{2-10}$-alkene, preferably, $C_{2-6}$-alkene, more preferably ethylene, 1-propylene or 2-propylene, wherein said substituents are one more groups selected from the group consisting of chlorine, fluorine, bromine or phenyl;
i) $C_{1-10}$-alkoxycarbonyl, preferably, $C_{1-6}$-alkoxycarbonyl, more preferably, methoxycarbonyl or t-butoxycarbonyl;
j) $C_{1-10}$-alkoxycarbamido, preferably, $C_{1-6}$-alkoxycarbamido, more preferably, methoxycarbamido, ethoxycarbamido or n-propoxycarbamido;
k) N-$C_{1-10}$-alkoxy-N-$C_{1-10}$-alkylaminocarbonyl, preferably, N-$C_{1-6}$-alkoxy-N-$C_{1-6}$-alkylaminocarbonyl, more preferably, N-methoxy-N-methylaminocarbonyl, N-ethoxy-N-methylaminocarbonyl, N-methoxy-N-ethylaminocarbonyl or N-ethoxy-N-ethylaminocarbonyl;
l) halo-$C_{1-10}$-alkyl, preferably, halo-$C_{1-6}$-alkyl, more preferably, chloromethyl, 1-chloroethyl or 2-chloroethyl;
m) $C_{6-10}$-aryl group, preferably, phenyl, tolyl, anisoyl, mesityl, and xylyl;

4 n) substituted $C_{1-10}$-alkyl, preferably, phenyl, tolyl, anisoyl, mesityl, and xylyl, wherein said substituents are one or more groups selected from the group consisting of ethyl, n-propyl, isopropyl, amino, methylamino and dimethylamino; and,
o) —COOH or —COOY, wherein Y is a pharmaceutically acceptable cation, preferably, sodium, potassium, calcium or any other pharmaceutically acceptable cation known in the art; and, $R_2$ is selected from the group consisting of
1) —COOH;
2) Cl or F;
3) trifluoromethyl;
4) —CHO; and,
5) —$CH_2M$, wherein M is selected from the group consisting of
   a) hydrogen;
   b) halo, preferably F, Cl, Br, or I;
   c) hydroxy;
   d) $C_{1-10}$-alkoxy, preferably, $C_{1-6}$-alkoxy, more preferably, methoxy, ethoxy, n-propoxy or isopropoxy;
   e) $C_{6-10}$-aryloxy, preferably, $C_{6-10}$-aryloxy, more preferably, phenoxy or naphthoxy;
   f) $C_{6-10}$-aryl-$C_{1-10}$-alkoxy, preferably, $C_{6-10}$-aryl-$C_{1-6}$-alkoxy, more preferably, phenylmethoxy, 1-phenylethoxy or 2-phenylethoxy;
   g) mercapto, preferably, thiol;
   h) substituted mercapto, preferably, thiol, wherein said substituents are selected from the group consisting of methyl, ethyl or phenyl;
   i) $C_{2-10}$-acylthio, preferably $C_{2-6}$-acylthio, more preferably, acetylthio or propanoylthio;
   j) $C_{2-10}$-acyloxy or carbamoyloxy, preferably, $C_{2-6}$-alkanoyloxy, $C_{6-10}$-aryl-carbonyloxy, carbamoyloxy or thiocarbamoyloxy, more preferably, acetoxy or benzoyloxy;
   k) substituted $C_{2-10}$-acyloxy or carbamoyloxy, preferably, $C_{2-6}$-alkanoyloxy, $C_{6-10}$-arylcarbonyloxy, N-$C_{1-6}$-alkylcarbamoyloxy, N,N-di-$C_{1-6}$-alkylcarbamoyloxy, thiocarbamoyloxy, N-$C_{1-6}$-alkylthiocarbamoyloxy or N,N-di-$C_{1-6}$-alkylthiocarbamoyloxy, more preferably, acetoxy, α-aminophenylacetoxy, benzoyloxy, benzyloxycarbonyloxy, succinoyloxy, N-methylcarbamoyloxy, N-ethylcarbamoyloxy, N,N-dimethylcarbamoyloxy, N,N-diethylcarbamoyloxy, N-methylthiocarbamoyloxy, N-ethylthiocarbamoyloxy, N,N-dimethylthiocarbamoyloxy, N,N-diethylthiocarbamoyloxy, wherein said substituents are one or more groups selected from the group consisting of —COOH, aminophenyl, phenyl, methyl, ethyl, chlorine, bromine or fluorine;
   l) a quaternary ammonium salt, preferably trimethyl ammonium chloride or triethyl ammonium chloride;
   m) amino or amido group, preferably —$NH_2$ or —$CONH_2$; and,
   n) substituted amino or amido group, preferably —$NH_2$ or —$CONH_2$, wherein said substituents are one or two $C_{1-10}$-alkyl groups, preferably $C_{1-6}$-alkyl groups, more preferably, methyl, ethyl, n-propyl, isopropyl or n-butyl;

$R_3$ is selected from the group consisting of
a) hydrogen; and,
b) pharmaceutically acceptable cations, preferably, sodium, potassium or calcium.

In a preferred embodiment, n is 0 and $R_1$ is selected from the group consisting of t-butyl, bromine and hydrogen.

In a more preferred embodiment, n is 0, $R_1$ is selected from the group consisting of t-butyl, bromine and hydrogen and $R_2$ is —$CH_2OAc$.

In another preferred embodiment, n is 1 and $R_1$ is selected from the group consisting of t-butyl, bromine and hydrogen.

In another more preferred embodiment, n is 1, $R_1$ is selected from the group consisting of t-butyl, bromine and hydrogen and $R_2$ is —$CH_2OAc$.

In a most preferred embodiment, n is 1, $R_1$ is t-butyl, $R_2$ is —$CH_2OAc$ and $R_3$ is sodium.

The compounds of this invention are generally prepared from 7-aminocephalosporanic acid. Their preparation is as follows. Chiral 7-aminocephalosporanic acid, 2, was esterified with diphenyldiazomethane to obtain 3. Treatment of 3 with excess triethylamine and trifluoromethanesulfonic anhydride, followed by hydrolysis of the resultant trifluorosulfonyl imine produced benzhydryl 7-oxocephalosporanate 4. Due to its instability, this ketone was used without further purification. The reaction between 4 and ethynylmagnesium bromide stereospecifically produced the corresponding propargylic alcohol 5. Conversion to the triflate 6 with trifluoromethanesulfonic anhydride, followed by careful treatment with either (t-$C_4H_9$)$_2$CuCNLi$_2$ or with copper(I) bromide, yielded either benzhydryl 7-(2'α-t-butylvinylidene) cephalosporanate 7 or benzhydryl 7-(2'α-bromovinylidene) cephalosporanate 8, respectively. The synthesis of these chiral allenes proceeded with 100% stereospecificity via an anti $S_N2'$ displacement of the leaving group. Reduction of 8 with the Zn-Cu couple produced the parent terminally unsubstituted benzhydryl 7-vinylidene cephalosporanate 9, as shown below.

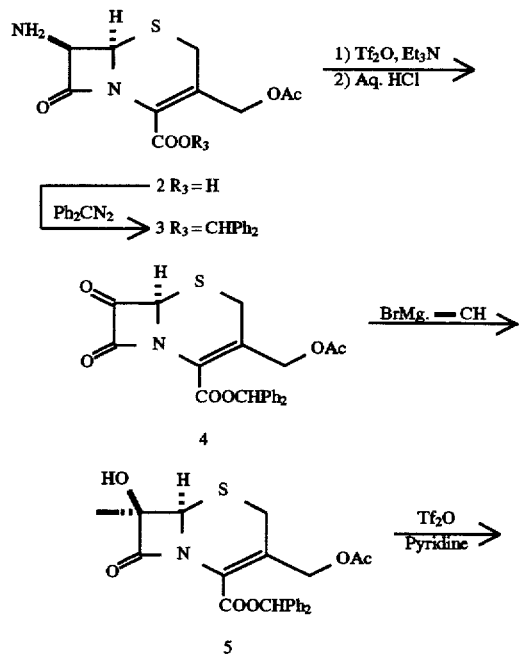

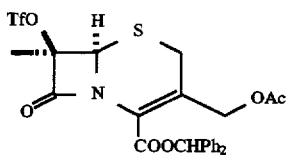

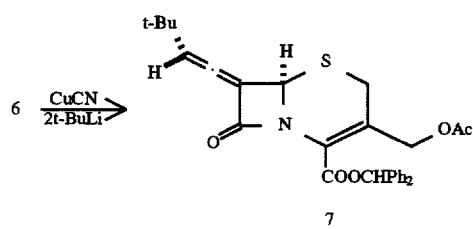

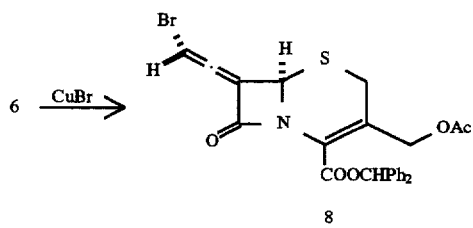

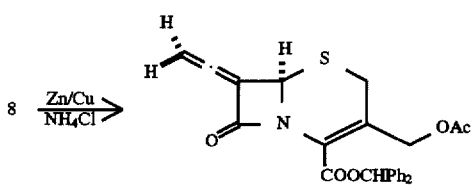

Deprotection of compounds 7, 8, and 9 produced the corresponding sodium salts 13, 14, and 15, respectively. Sulfones 10, 11, and 12 were synthesized by oxidation of 7, 8, and 9 with excess m-chloroperbenzoic acid (m-CPBA). Sodium salts 16 and 17 could be obtained by the deprotection of sulfones 10 and 12, respectively. The reaction scheme is shown below.

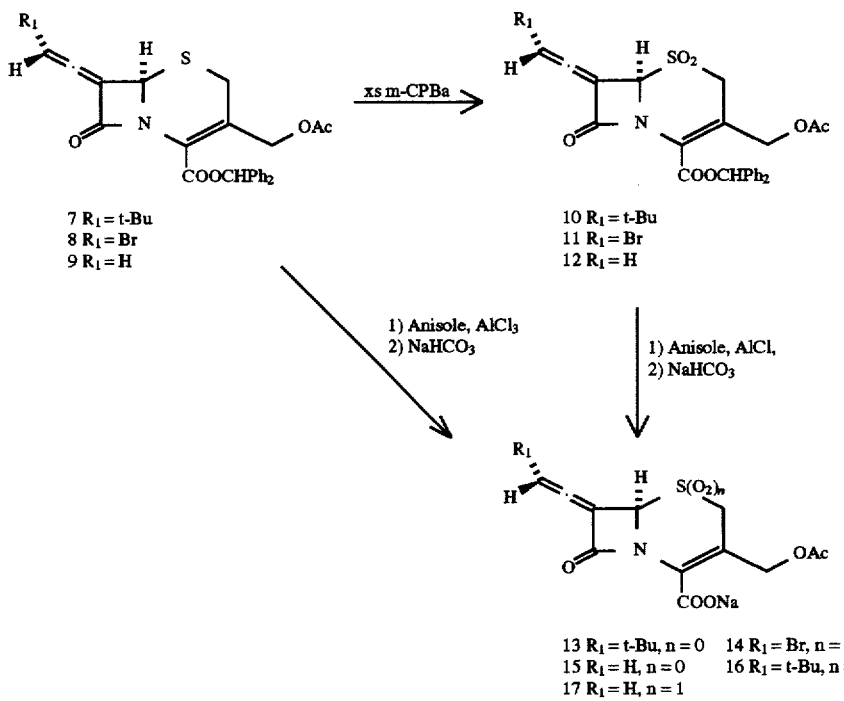

Compounds having $R_1$ groups other than those shown above may be made by forming a vinylidene anion and reacting it with an electrophile. The vinylidene anion may be made by a standard lithium-halogen (or magnesium-halogen) exchange reaction, for example, reaction of 14 with methyl lithium. The lithium vinylidene may then be functionalized by reaction with an electrophile, for example, an alkoxycarbonyl chloride, a N-alkoxy-N-alkylaminocarbonyl chloride, a dihaloalkyl, an epoxide (to form a hydroxyalkyl), or carbon dioxide.

The compounds wherein $R_1$ is alkoxy, alkanoyloxy, alkene, alkoxycarbamido or aryl may be made by a nucleophilic attack of an appropriate anion (i.e., alkoxide, alkanoyloxide, alkenyl anion, alkyoxycarbamidyl anion, or aryl anion) on the propargylic triflate 6. Thus, sodium methoxide may be used to add to compound 6 to form the 7-methoxy-vinylidene.

The compounds wherein $R_2$ is a halogen may be formed by displacement of the —OAc group with ethylxanthate (EtOCS$_2$K). Raney-Nickel desulfurization (H$_2$/Ra-Ni) would yield the exocyclic alkene which may then be ozonized to the 3-hydroxy cephem. Reaction with a halogenating reagent would provide the 3-halo species. For example, PCl$_5$ may be used to convert the 3-OH group into a 3-Cl group. The 3-methyl species may be obtained by the rearrangement of the exocyclic alkene, formed by Raney-Nickel desulfurization, by reaction with Et$_3$N. The 3-hydroxymethyl species may be obtained by hydrolysis of the —OAc group with NaOH or an appropriate enzyme. The 3-halomethyl species may be formed by reaction of the 3-hydroxymethyl species with a halogenating reagent. For example, PCl$_5$ may be used to form the 3-chloromethyl species.

The compounds wherein M is alkoxy, aryloxy, or arylalkoxy may be obtained by reaction of the 3-hydroxymethyl species with tosyl chloride and displacement of the resultant tosylate with an oxide. For example, sodium methoxide may be used to obtain the 3-methoxymethyl species. The compounds wherein M is mercapto may be formed by reaction of the 3-chloromethyl compound with sodium sulfhydride (NaSH). This compound may be further derivatized with an alkylhalide to form a substituted mercapto or an acylchloride to form an acylthio group.

The species wherein M is an amino group may be formed by the Gabriel Synthesis, i.e., reaction of the 3-chloromethyl compound with potassium phthalimide and hydrolysis of the product with acid to yield the 3-aminomethyl compound. The 3-ammoniomethyl compound may be formed by reaction of the 3-aminomethyl compound with methyl chloride to form the 3-trimethylammoniomethyl chloride.

The compound wherein M is an amido group (CONH$_2$) may be formed by displacement of the tosylate described above with cyanide, e.g., KCN, followed by hydrolysis of the resulting nitrile to the amide.

The activity of the present compounds against β-lactamases was determined by measuring the IC$_{50}$. The IC$_{50}$ value represents the concentration of inhibitor required to effect a 50% loss of activity of free enzyme. The present 7-vinylidenecephems were evaluated as inhibitors of the β-lactamase of *Enterobacter cloacae* P99. The IC$_{50}$ value of each compound was determined as follows. Following a 10 minute incubation of a dilute solution of enzyme (2.56 nM) and inhibitor (<0.64 mM), a 50 mL aliquot of this incubation mixture was then further diluted into 1 mL nitrocefin solution, and the rate of hydrolysis was measured during a 1 minute period by monitoring the absorbance of nitrocefin as a function of time. The present 7-vinylidenecephems were evaluated relative to known inhibitors tazobactam, clavulanic acid and 6-(2'α-t-butylvinylidene) penam sulfone. The results are summarized in Table 1 below.

TABLE 1

P99 β-lactamase inhibitory activity

| Compound | $IC_{50}$ (mg/mL) |
| --- | --- |
| 7-(2'α-t-butylvinylidene) cephem (13) | 3.91 |
| 7-(2'α-t-butylvinylidene) cephem sulfone(16) | 0.05 |
| 7-(2'α-t-butyl-2'β-deuteriovinylidene) cephem sulfone (21) | 0.10 |
| 7-vinylidenecephem (15) | 25.83 |
| 7-vinylidenecephem sulfone (17) | 0.11 |
| 6-(2'α-t-butylvinylidene) penam sulfone | 0.39 |
| 7-(2'α-bromovinylidene) cephem (14) | 6.16 |
| Tazobactam | 0.22 |
| Clavulanic acid | 17.24 |

The compounds of the formula I are surprisingly potent inhibitors of β-lactamase, particularly β-lactamase of the class C. All of compounds made according to this formula are found to have $IC_{50}$ values competitive with commercially available clavulanic acid, and several of the compounds are competitive with commercially available tazobactam. Compound (16) 7-(2'α-t-butylvinylidene)cephem sulfone was found to be the most potent inhibitor, approximately five-fold better than tazobactam and 350-fold better than clavulanic acid. Thus the compounds of the formula I are useful as β-lactamase inhibitors.

In a second embodiment, the present invention provides pharmaceutical compositions useful for inhibiting a β-lactamase. The present pharmaceutical compositions comprise at least one of the present 7-vinylidene cephalosporins and at least one pharmaceutically acceptable carrier.

The present compositions may be employed in capsule form or as tablets, powders or liquid solutions or as suspensions or elixirs. They may be administered orally, intravenously or intramuscularly. The present compositions are preferably presented in a form suitable for absorption by the gastrointestinal tract.

Tablets and capsules for oral administration may be in unit dose presentation form, and may contain conventional pharmaceutical carriers such as binding agents, for example, syrup, acacia, gelatin, sorbitol, tragacanth, or polyvinylpyrrolidone; fillers, for example, lactose, sugar, maize-starch, calcium phosphate, sorbitol or glycine, lubricants, for example, magnesium stearate, talc, polyethylene glycol, silica; disintegrants, for example, potato starch; or acceptable wetting agents such as sodium lauryl sulphate. The tablets may be coated according to methods well known in the art. Oral liquid preparations may be in the form of aqueous or oily suspensions, solutions, emulsions, syrups, elixirs, etc. or may be presented as a dry product, for reconstruction with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible fats; emulsifying agents, for example lecithin, sorbitan monooleate or acacia; non-aqueous vehicles, which may include edible oils, for example, almond oil, fractionated coconut oil, oily esters, propylene glycol, or ethyl alcohol; preservatives, for example, methyl or propyl p-hydroxybenzoates or sorbic acid. Suppositories will contain conventional suppository bases, e.g., cocoa butter or other glyceride.

Compositions for injection may be presented in unit does form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The present compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops, etc. Topical applications may be formulated in hydrophobic or hydrophilic bases as ointments, creams, lotions, paints, powders, etc.

Also, in addition to a carrier, the present compositions may include other ingredients such as stabilizers, binders, antioxidants, preservatives, lubricators, suspending agents, viscosity agents or flavoring agents and the like.

For veterinary medicine, the composition may, for example, be formulated as an intramammary preparation in either long acting or quick-release bases.

The dosage to be administered depends to a large extent upon the condition of the subject being treated and the weight of the subject, the route and frequency of administration, the parenteral route being preferred for generalized infections and the oral route for intestinal infections.

The instant compositions may be administered in several unit dosage forms as, for example, in solid or liquid orally ingestible dosage form. The compositions per unit dosage, whether liquid or solid may contain from 0.1% to 99% of active material (the present 7-vinylidene cephalosporins and optional antibiotic), the preferred range being from about 10–60%. The composition will generally contain from about 15 mg to about 1500 mg by weight of active ingredient based upon the total weight of the composition; however, in general, it is preferable to employ a dosage amount in the range of from about 250 mg to 1000 mg. In parenteral administration the unit dosage is usually the pure compound in a slightly acidified sterile water solution or in the form of a soluble powder intended for solution.

The present β-lactamase inhibitors will be particularly useful in the treatment of infections caused by Enterobacter, Citrobacter, and Serratia. These bacteria have the ability to attach to the epithelial cells of the bladder or kidney (causing urinary tract infections) and are resistant to multiple antibiotics including amoxicillin and ampicillin. The present β-lactamase inhibitors would also be useful in the treatment of infections caused by highly resistant Pneumococci. Such diseases include otitis media, sinusitis, meningitis (both in children and adults), bacteremia, and septic arthritis. Resistant pneumococcal strains have surfaced in many parts of the world. For example, in Hungary, 58% of *S. pneumoniae* are resistant to penicillin, and 70% of children who are colonized with *S. pneumonniae* carry resistant strains that are also resistant to tetracycline, erythromycin, trimethoprin/sulfamethoxazole (TMP/SMX), and 30% resistant to chloroanphenicol. *Klebsiella pneumoniae* (resistant via the production of β-lactamase) have caused hospital outbreaks of wound infection and septicemia.

Thus, in a third embodiment, the present invention provides pharmaceutical compositions with increased β-lactam antibiotic activity. This pharmaceutical composition is as defined above, but in addition to at least one of the present 7-vinylidene cephalosporins and at least one a pharmaceutically acceptable carrier, the compositions also contains at least one β-lactam antibiotic. The β-lactam antibiotic may be any of the above-noted antibiotics or any other known in the art, preferably amoxicillin or piperacillin, and its selection will depend upon what indication is necessary.

In a fourth embodiment, the present invention provides a method of inhibiting a β-lactamase, comprising administering to a patient in need thereof an effective amount of at least one of the present 7-vinylidene cephalosporins. The method of administration may be any of the above-noted methods or any other known to one of skill in the art.

In a fifth embodiment, the present invention provides a method of enhancing the biological activity of a β-lactam antibiotic by coadministering to a patient in need thereof, an effective amount of one of the present 7-vinylidene cephalosporins and an effective amount of at least one β-lactam antibiotic. The method of administration may be any of the above-noted methods or any other known to one of skill in the art. The β-lactam antibiotic may be any of the above-noted β-lactam antibiotics or any other known in the art.

Other features of the invention will become apparent in the course of the following descriptions of exemplary embodiments which are given for illustration of the invention and are not intended to be limiting thereof.

EXAMPLES

EXAMPLE 1

Benzhydryl 7β-Aminocephalosporanate (3)

The title compound was prepared according to the procedure of Sheehan and Commons. To a suspension of 7-aminocephalosporanic acid, 2, (130.4 g, 0.48 mol) in methanol (480 mL) was added a solution of diphenyldiazomethane (93.0 g, 0.48 mol) in $CH_2Cl_2$. The suspension was stirred (mechanically) at room temperature for 44 hours. The solid was removed by filtration, the organic layer was concentrated in vacuo and purified by column chromatography (10% $CH_3OH$ in $CH_2Cl_2$) to afford the desired ester as a pale yellow solid (86.1 g, 41% yield). $R_f$=0.44 in 1:9 $CH_3OH:CH_2Cl_2$; mp 45°–46° C.; IR ($CHCl_3$) 2980, 1780, 1730 cm$^{-1}$; $^1H$ NMR ($CDCl_3$) δ 8.41 (2H, bs), 7.22 (10H, m), 6.91 (1H, s), 5.27 (1H, d, J=2.8 Hz), 5.15 (1H, d, A of ABq, J=14.0 Hz), 4.94 (1H, s), 4.84 (1H, d, B of ABq, J=14.0 Hz), 3.73 (1H, d, A of ABq, J=16.7 Hz), 3.33 (1H, d, B of ABq, J=16.7 Hz), 1.92 (3H, s); $^{13}C$ NMR ($CDCl_3$) δ 169.8, 168.8, 160.6, 138.9, 138.7, 129.5, 129.3, 129.1, 128.7, 128.5, 127.97, 127.61, 127.52, 127.18, 126.52, 126.06, 125.4, 79.0, 63.3, 62.6, 58.5, 25.7, 20.1.

EXAMPLE 2

Benzhydryl 7-Oxocephalosporanate

The title compound was prepared by modifying the procedure of Hagiwara, D. F.; Sawada, K.; Ohnami, T.; Aratani, M.; Hashimoto, M. *J. Chem Soc. Chem. Commun.* 1982, 578. To a solution of benzhydryl 7β-aminocephalosporanate, 3, (5.9 g, 13.5 mmol) in anhydrous $CH_2Cl_2$ (70 mL) at −78° C., triethylamine (5.6 mL, 40.4 mmol) was added dropwise with stirring. After 5 minutes, trifluoromethane-sulfonic anhydride (6.8 mL, 40.4 mmol) was added dropwise to this solution over a 5 minute period. The reaction mixture was allowed to warm slowly to 0° C. over a 1 hour period. It was then cooled to −78° C. and triethylamine (5.6 mL, 40.4 mmol) was added over approximately 5 minutes. The reaction mixture was stirred at −78° C. for an additional 30 minutes, followed by the addition of 0.5N HCl (50 mL). The cooling bath was removed and the resultant solution was further stirred for 30 minutes. The layers were separated and the aqueous layer was extracted with $CH_2Cl_2$ (50 mL). The combined organic layers were washed with cold phosphate buffer, pH 5.7 (5×200 mL), dried ($Na_2SO_4$), and concentrated to produce the title compound (5.8 g, 98% yield) as a pale yellow solid which was used without further purification. IR ($CHCl_3$) 3005, 1830, 1790, 1740 cm$^{-1}$; $^1H$ NMR ($CDCl_3$) δ 7.39 (10H, m), 7.05 (1H, s), 5.07 (1H, d, A of ABq, J=13.9 Hz), 4.85 (1H, d, B of ABq, J=14.0 Hz), 3.64 (1H, d, A of ABq, J=18.5 Hz), 3.44 (1H, d, B of ABq, J=18.6 Hz), 2.05 (3H, s); $^{13}C$ NMR ($CDCl_3$) δ 188.4 (s), 170.3 (s), 160.1 (s), 158.7 (s), 138.8 (s), 138.6 (s), 128.4, 128.2, 128.1, 127.7, 126.9, 126.2, 80.1 (d), 65.8 (d), 62.6 (t), 27.7 (t), 20.4 (q).

EXAMPLE 3

Benzhydryl 7α-Ethynyl-7β-hydroxycephalosporanate (5)

Ethynylmagnesium bromide (45.2 mL, 22.6 mmol) was slowly added to a cold (−78° C.) solution of 7-oxocephalosporanate, 4, (5.5 g, 12.6 mmol) in anhydrous THF (85 mL). It was then stirred at −78° C. for 1 hour and at −40° C. for 1.5 hours. The reaction mixture was quenched with acetic acid (2.9 mL, 50.4 mmol) and ether (500 mL) was added. The combined organic layers were washed with water (1×100 mL), brine (1×100 mL), dried ($Na_2SO_4$), and concentrated in vacuo. The product was immediately purified by column chromatography (1:4 $EtOAc:CH_2Cl_2$) to give the title compound (2.9 g, 50% yield) as pale yellowish fluffy solid. $R_f$=0.56 in 1:4 $EtOAc:CH_2Cl_2$; mp 50°–52° C.; IR ($CHCl_3$) 3670, 3565, 3300, 3010, 2120, 1790, 1730 cm$^{-1}$; $^1H$ NMR ($CDCl_3$) δ 7.37 (10H, m), 6.95 (1H, s), 5.14 (1H, d, A of ABq, J=13.9 Hz), 5.08 (1H, s), 4.89 (1H, d, B of ABq, J=13.9 Hz), 3.53 (1H, d, A of ABq, J=17.8 Hz), 3.35 (1H, d, B of ABq, J=17.8 Hz), 2.88 (1H, s), 2.05 (3H, s); $^{13}C$ NMR ($CDCl_3$) δ 170.7 (s), 162.7 (s), 160.3 (s), 139.3 (s), 139.1 (s), 132.1 (s), 128.42, 128.0, 127.3, 126.9, 125.6, 79.6 (d), 78.3 (s), 77.9 (s), 77.3 (d), 65.4 (d), 62.6 (t), 26.3 (t), 20.5 (q). Anal. Calcd for $C_{25}H_{21}NO_6S$: C, 64.79; H, 4.54; N, 3.02. Found: C, 64.20; H, 4.39; N, 3.25.

EXAMPLE 4

Benzhydryl 7α-Ethynyl-7β-trifluoromethanesulfonato Cephalosporanate (6)

Trifluoromethanesulfonic anhydride (3.3 mL, 19.1 mmol) was added dropwise (4 s intervals) to a cold (0° C.) solution of pyridine (2.6 mL, 31.8 mmol) and benzhydryl 7α-ethynyl-7β-hydroxycephalosporanate, 5, (5.9 g, 12.7 mmol) in anhydrous $CH_2Cl_2$ (60 mL). The reaction mixture was allowed to warm to room temperature and monitored by TLC (reaction time=30 minutes). After concentration the residue was purified by column chromatography ($CH_2Cl_2$) to yield the title compound as a white solid (4.67 g, 62% yield). $R_f$=0.63 in 15% EtOAc in $CH_2Cl_2$; mp 42°–43° C.; IR ($CHCl_3$) 3300, 3020, 2120, 1810, 1780, 1750 cm$^{-1}$; $^1H$ NMR ($CDCl_3$) δ 7.39 (10H, m), 6.94 (1H, s), 5.29 (1H, d, A of ABq, J=13.9 Hz), 5.26 (1H, s), 5.09 (1H, d, B of ABq, J=14.8 Hz), 3.52 (1H, d, A of ABq, J=16.5 Hz), 3.34 (1H, d, B of ABq, J=18.3 Hz), 3.29 (1H, s), 2.09 (3H, s); $^{13}C$ NMR ($CDCl_3$) δ 170.1 (s), 159.4 (s), 155.1 (s), 140.8 (s), 139.2 (s), 139.1 (s), 128.5, 128.1, 126.9, 126.8, 125.3, 118.0 (q, J=321.11 Hz), 87.3 (s), 84.0 (d), 79.6 (d), 71.9 (s), 66.5 (d), 61.7 (t), 26.5 (t), 20.4 (q). Anal. Calcd for $C_{26}H_{20}NO_8S_2F_3$: C, 52.44; H, 3.36; N, 2.35; F, 9.58. Found: C, 52.66; H, 3.37; N, 2.33; F, 9.26.

EXAMPLE 5

Benzhydryl 7-(2'α-bromovinylidene) Cephalosporanate (8)

Method A: Copper (I) bromide (CuBr, 133 mg, 0.93 mmol) was added in one portion to a solution of benzhydryl 7α-ethynyl-7β-(trifluoromethanesulfonato) cephalosporanate, 6, (500 mg, 0.84 mmol) in anhydrous DMF (5.0 mL) at room temperature and stirred in the dark for 30 minutes. The DMF was removed in vacuo at room temperature. The residue was dissolved in ether (50 mL), washed with water (2×15 mL), dried ($Na_2SO_4$), and concentrated to produce a yellow solid. This material was purified by column chromatography ($CH_2Cl_2$) to yield the title compound as a pale yellow solid (140 mg, 32% yield). $R_f$=0.75 in 15% EtOAc in $CH_2Cl_2$; mp 63°–65° C.; IR ($CHCl_3$) 3010, 1950, 1780, 1730 $cm^{-1}$; $^1H$ NMR ($CDCl_3$) δ 7.42 (10H, m), 7.01 (1H, s), 6.74 (1H, d, J=1.17 Hz), 5.38 (1H, d, J=1.12 Hz), 5.02 (1H, d, A of ABq, J=13.5 Hz), 4.78 (1H, d, B of ABq, J=13.4 Hz), 3.60 (1H, d, A of ABq, J=18.31 Hz), 3.41 (1H, d, B of ABq, J=18.11 Hz), 2.04 (3H, s); $^{13}C$ NMR ($CDCl_3$) δ 194.6 (s), 170.3 (s), 160.6 (s), 156.1 (s), 139.1 (s), 138.9 (s), 128.4, 128.1, 128.0, 127.7, 127.1, 124.6, 111.7 (s), 81.8 (d), 79.9 (d), 62.9 (t), 56.2 (d), 27.8 (t), 20.5 (q); HRMS calcd for $[C_{25}H_{20}NO_5SBrNa]^+$, i.e. $[M+Na]^+$, m/z calcd 548.0143, found 548.0146.

Method B: Lithium bromide (LiBr, 285 mg, 3.3 mmol), and copper (I) bromide (CuBr, 470 mg, 3.3 mmol) were added in one portion to a solution of benzhydryl 6α-ethynyl-6β-(trifluoromethanesulfonato) cephalosporanate, 6, (1.5 g, 2.5 mmol) in anhydrous THF (15 mL). The mixture was allowed to stir at room temperature for 5 minutes. The THF was removed in vacuo. The residue was dissolved in ether (20 mL), washed with water (1×10 mL), dried ($Na_2SO_4$), and concentrated in vacuo to give yellow solid (1.30 g, 98% yield). This reaction produced a single isomer 7-(2'α-bromovinylidene) cephalosporanate. The material was judged to be 95% pure by $^1H$ NMR and used for next step without purification.

EXAMPLE 6

Benzhydryl 7-Vinylidenecephalosporanate (9)

To a solution of benzhydryl 7-(2'α-bromovinylidene) cephalosporanate, 8, (2.4 g, 4.6 mmol) in a 1:5 mixture of anhydrous THF:MeOH (60 ml) was added $NH_4Cl$ (0.98 g, 18.4 mmol) and Zn-Cu couple (0.6 g, 9.2 mmol). After stirring at room temperature for 30 minutes, the reaction mixture was concentrated in vacuo. The residue was dissolved in ether (100 mL), washed with water (20 mL), dried ($Na_2SO_4$), concentrated, and chromatographed (1:1 Hexane:$CH_2Cl_2$ followed by 1:3 Hexane:$CH_2Cl_2$) to give a white fluffy solid (1.45 g, 71% yield). $R_f$=0.3 in $CH_2Cl_2$; IR ($CHCl_3$) 3010, 1985, 1790, 1730 $cm^{-1}$; $^1H$ NMR ($CDCl_3$) δ 7.40 (10H, m), 7.0 (1H, s), 5.58 (2H, d, J=13.4 Hz), 5.29 (1H, t, J=1.88 Hz), 4.99 (1H, d, A of ABq, J=13.35 Hz), 4.74 (1H, d, B of ABq, J=13.3 Hz), 3.57 (1H, d, A of ABq, J=18.2 Hz), 3.37 (1H, d, B of ABq, J=18.3 Hz), 2.03 (3H, s); $^{13}C$ NMR ($CDCl_3$) δ 200.0 (s), 170.3 (s), 160.8 (s), 158.7 (s), 139.2 (s), 139.0 (s), 128.4, 128.0, 127.9, 127.7, 127.4, 127.0, 123.0, 105.7 (s), 85.1 (t), 79.7 (d), 63.0 (t), 56.6 (d), 27.8 (t), 20.5 (q); HRMS calcd for $[C_{24}H_{21}NO_5SNa]^+$, i.e. $[M+Na]^+$, m/z calcd 470.1038, found 470.1042.

EXAMPLE 7

Benzhydryl 7-(2'α-t-Buytlvinylidene) Cephalosporanate (7)

To a suspension of CuCN (0.376 g, 4.2 mmol) in anhydrous THF (30 mL) was added t-BuLi (4.0 mL, 1.7M in pentane, 6.8 mmol) at −100° C. The cooling bath was removed until all the solid had gone into the solution (approximately 3 minutes). This solution was again cooled to −100° C. and was cannulated into a cold (−100° C.) solution of benzhydryl 7α-ethynyl-7β-(trifluoromethanesulfonato) cephalosporanate, 6, (2.0 g, 3.4 mmol) in anhydrous THF (5 mL) at −100° C. The solution was further stirred at −100° C. for 1 minute before pouring the cold reaction mixture into cold (0° C.) saturated $NH_4Cl$ solution (100 mL). The reaction mixture was extracted with ether (2×50 mL), dried ($Na_2SO_4$), concentrated, and chromatographed (5% EtOAc in $CH_2Cl_2$) to give a white fluffy solid (0.913 g, 54% yield). $R_f$=0.80 in 5% EtOAc in $CH_2Cl_2$; mp 113°–114° C.; IR ($CHCl_3$) 3000, 2960, 1970, 1770, 1730 $cm^{-1}$; $^1H$ NMR ($CDCl_3$) δ 7.42 (10H, m), 7.05 (1H, s), 5.98 (1H, d, J=1.63 Hz), 5.25 (1H, d, J=1.69 Hz), 4.97 (1H, d, A of ABq, J=13.30 Hz), 4.72 (1H, d, B of ABq, J=13.23 Hz), 3.55 (1H, d, A of ABq, J=18.14 Hz), 3.35 (1H, d, B of ABq, J=18.23 Hz), 2.01 (3H, s), 1.18 (9H, s); $^{13}C$ NMR ($CDCl_3$) δ 194.6 (s), 170.2 (s), 161.1 (s), 159.5 (s), 139.2 (s), 139.0 (s), 128.3,128.0,127.9, 127.7, 127.1, 121.9, 113.2 (d), 107.2 (s), 79.6 (d), 63.0 (t), 57.0 (d), 33.6 (s), 29.7 (q), 27.8 (t), 20.5 (q). Anal. Calcd for $C_{29}H_{29}NO_5S$: C, 69.18; H, 5.77; N, 2.78. Found: C, 69.08; H, 6.00; N, 2.73.

EXAMPLE 8

Benzhydryl 7-(2'α-Bromovinylidene) Cephalosporanate Sulfone (11)

To the solution of sulfide 8 (0.65 g, 1.23 mmol) in $CH_2Cl_2$ (10 mL) and pH=6.4 phosphate buffer solution (10 mL), was added in one portion m-CPBA (85%, 0.853 g, 4.94 mmol). The mixture was stirred as rapidly as possible overnight at room temperature. After separating the layers, the aqueous layer was extracted with ether (1×10 mL). The combined organic layers were washed with 5% $NaHSO_3$ (1×5 mL), saturated $NaHCO_3$ (1×5 mL), dried ($Na_2SO_4$), concentrated, and chromatographed 5% EtOAc in $CH_2Cl_2$. There was obtained a yellow solid (0.32 g, 46% yield). $R_f$=0.35 in 5% EtOAc in $CH_2Cl_2$; IR ($CHCl_3$) 3020, 1950, 1800, 1740, 1350, 1130 $cm^{-1}$; $^1H$ NMR ($CDCl_3$) δ 7.39 (10H, m), 7.00 (1H, s), 6.94 (1H, d, J=1.38 Hz), 5.39 (1H, d, J=1.13 Hz), 5.09 (1H, d, A of ABq, J=14.25 Hz), 4.75 (1H, d, B of ABq, J=14.33 Hz), 4.06 (1H, d, A of ABq, J=18.25 Hz), 3.82 (1H, d, B of ABq, J=18.17 Hz), 2.06 (3H, s); $^{13}C$ NMR ($CDCl_3$) δ 196.8, 170.1, 159.6, 155.3, 138.7, 138.6, 128.6, 128.4, 128.3, 127.6, 127.1, 125.8, 125.4, 104.4, 83.8, 80.6, 69.0, 61.9, 51.3, 20.4.

EXAMPLE 9

Benzhydryl 7-Vinylidene Cephalosporanate Sulfone (12)

This compound was prepared from the sulfide 9 as described for the benzhydryl 7-(2'α-bromovinylidene) cephalosporanate sulfone (11) (Example 8) (yield=55%, 0.590 g). $R_f$=0.35 in 5% EtOAc in $CH_2Cl_2$; mp 155°–156° C.; IR ($CHCl_3$) 3010, 1985, 1790, 1730, 1340, 1125 $cm^{-1}$; $^1H$ NMR ($CDCl_3$) δ 7.43 (10H, m), 6.99 (1H, s), 5.70 (2H, dd, J=1.65 Hz, J=5.31 Hz), 5.33 (1H, s), 5.03 (1H, d, A of ABq, J=14.02 Hz), 4.70 (1H, d, B of ABq, J=14.01 Hz), 4.04 (1H, d, A of ABq, J=8.12 Hz), 3.79 (1H, d, B of ABq, J=18.40 Hz), 2.03 (3H, s); $^{13}C$ NMR ($CDCl_3$) δ 201.7 (s), 170.1 (s), 159.8 (s), 157.6 (s), 138.8 (s), 138.6 (s), 128.4, 128.2, 128.1, 127.5, 127.0, 124.0, 98.8 (s), 86.4 (t), 80.3 (d), 69.5 (d), 61.9 (t), 51.0 (t), 20.3 (q); HRMS calcd for $[C_{25}H_{21}NO_7SNa]^+$, i.e. $[M+Na]^+$, m/z calcd 502.0936, found 502.0931.

EXAMPLE 10

Benzhydryl 7-(2'α-t-butylvinylidene) Cephalosporanate Sulfone (10)

This compound was prepared from the sulfide 7 as described above in benzhydryl 7-(2'α-bromovinylidene)

cephalosporanate sulfone (11) (Example 8) (yield=65%, 0.692 g). $R_f$=0.42 in 2% EtOAc in $CH_2Cl_2$; mp 163°–164° C.; IR ($CHCl_3$) 3010, 2960, 1970, 1790, 1740, 1340, 1125 $cm^{-1}$; $^1$H NMR ($CDCl_3$) δ 7.40 (10H, m), 7.01 (1H, s), 6.18 (1H, d, J=1.66 Hz), 5.30 (1H, s), 5.02 (1H, d, A of ABq, J=13.93 Hz), 4.68 (1H, d, B of ABq, J=13.93 Hz), 4.02 (1H, d, A of ABq, J=18.27 Hz), 3.76 (1H, d, B of ABq, J=18.20 Hz), 2.03 (3H, s), 1.19 (9H, s); $^{13}$C NMR ($CDCl_3$) δ 197.1 (s), 170.1 (s), 160.0 (s), 158.6 (s), 138.8 (s), 138.7 (s), 128.5, 128.3, 128.2, 127.6, 127.1, 126.5, 123.1, 114.6 (d), 100.1 (s), 80.4 (d), 70.1 (d), 62.0 (t), 51.2 (t), 34.0 (s), 29.7 (q), 20.4 (q); HRMS calcd for $[C_{29}H_{29}NO_7SNa]^+$, i.e. $[M+Na]^+$, m/z calcd 558.1562, found 558.1567.

EXAMPLE 11

Sodium Salt of 7-(2'α-Bromovinylidene) Cephalosporanic Acid (14)

To a solution of benzhydryl 7-(2'α-bromovinylidene)-cephalosporanate, 11, (300 mg, 0.57 mmol), in anhydrous $CH_2Cl_2$ (6 mL) was added anisole (0.62 mL, 5.7 mmol) at −78° C. followed by addition of $AlCl_3$ solution (1.43 mL, 1.0M in nitrobenzene, 1.43 mmol) in one portion. The mixture was stirred for 15 minutes at −78° C. and poured into rapidly stirred cold water (60 mL) containing $NaHCO_3$ (0.48 g, 5.7 mmol) followed by addition of EtOAc (50 mL). It was further stirred for 5 minutes and filtered using celite 545. The aqueous layer was separated and concentrated in vacuum to 2 mL and further purified by reverse phase preparative layer chromatography ($R_f$=0.62 in 5% EtOH in water). Lyophilization produced a pale yellow fluffy solid (105 mg, 48% yield). IR (nujol) 1975, 1750, 1610, 1410 $cm^{-1}$; $^1$H NMR ($d^6$-DMSO) δ 7.56 (1H, d, J=0.7 Hz), 5.62 (1H, s), 5.00 (1H, d, A of ABq, J=13.5 Hz), 4.76 (1H, d, B of ABq, J=13.28 Hz), 3.56 (1H, d, A of ABq, J=17.91 Hz), 3.17 (1H, d, B of ABq, J=17.84 Hz), 2.05 (3H, s); HRMS calcd for $[C_{12}H_9NO_5SBrNa_2]^+$, i.e. $[M+Na]^+$, m/z calcd 403.9180, found 403.9168.

EXAMPLE 12

Sodium Salt of 7-Vinylidene Cephalosporanic Acid (15)

This compound was prepared from the corresponding ester 9 (500 mg, 1.12 mmol) as described for the sodium salt of 7 -(2'α-bromovinylidene) cephalosporanic acid (14) above (Example 11) to give the title compound as a white fluffy solid (220 mg, 65% yield). $R_f$=0.65 in 5% EtOH in water. IR (nujol) 1980, 1760, 1735, 1590 $cm^{-1}$; $^1$H NMR ($d_6$-DMSO) δ 5.81 (2H, d, J=1.5 Hz), 5.41 (1H, s), 4.95 (1H, d, A of ABq, J=12.11 Hz), 4.71 (1H, d, B of ABq, J=12.0 5 Hz), 3.50 (1H, d, A of ABq, J=17.20 Hz), 3.24 (1H, d, B of ABq, J=17.40 Hz), 1.99 (3H, s); HRMS calcd for $[C_{12}H_{11}NO_5SNa]^+$, i.e. $[M+H]^+$, m/z calcd 304.0255, found 304.0250.

EXAMPLE 13

Sodium Salt of 7-(2'α-t-Butylvinylidene) Cephalosporanic Acid (13)

This compound was prepared from the corresponding ester 7 (420 mg, 0.83 mmol) as described in sodium salt of 7-(2'α-bromovinylidene) cephalosporanic acid (14) above (Example 11) to give title compound as a white fluffy solid (118 mg, 39% yield). $R_f$=0.80 in 15% EtOH in water. IR (nujol) 1975, 1760, 1720, 1610 $cm^{-1}$; $^1$H NMR ($d_6$-DMSO) δ 6.20 (1H, s), 5.33 (1H, s), 4.93 (1H, d, A of ABq, J=12.02 Hz), 4.69 (1H, d, B of ABq, J=11.97 Hz), 3.48 (1H, d, A of ABq, J=17.66 Hz), 3.20 (1H, d, B of ABq, J=18.09 Hz), 1.99 (3H, s), 1.10 (9H, s); HRMS calcd for $[C_{16}H_{19}NO_5SNa]^+$, i.e. $[M+H]^+$, m/z calcd 360.0881, found 360.0882.

EXAMPLE 14

Sodium Salt of 7-(2'α-t-Butylvinylidene) Cephalosporanic Acid Sulfone (16)

This compound was prepared from the corresponding ester 10 (250 mg, 0.47 mmol) as described in sodium salt of 7-(2'α-bromovinylidene) cephalosporanic acid (14) (Example 11) above to give the title compound as a white fluffy solid (110 mg, 60% yield). $R_f$=0.50 in 20% EtOH in water; IR (nujol) 1980, 1765, 1730, 1615, 1330, 1130 $cm^{-1}$. $^1$H NMR ($d_6$-DMSO) δ 6.39 (1H, s), 5.84 (1H, s), 4.92 (1H, d, A of ABq, J=12.07 Hz), 4.64 (1H, d, B of ABq, J=12.08 Hz), 4.05 (1H, d, A of ABq, J=17.71 Hz), 3.78 (1H, d, B of ABq, J=17.63 Hz), 1.99 (3H, s), 1.10 (9H, s); HRMS calcd for $[C_{16}H_{19}NO_7SNa]^+$, i.e. $[M+H]^+$, m/z calcd 392.0779, found 392.0780.

Obviously, numerous modifications and variations of the present invention are possible in light of the above teachings. It is, therefore, to be understood that within the scope of the appended claims, the invention may be practiced otherwise than as specifically described herein.

What is claimed as new and desired to be secured by Letters Patent of the United States is:

1. A method of enhancing the biological activity of a β-lactam antibiotic, comprising:

coadministering to a patient in need thereof an effective amount of a compound of the formula (1)

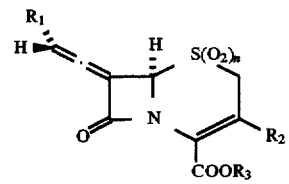

wherein n is 0 or 1;

$R_1$ is selected from the group consisting of
 a) hydrogen;
 b) linear or branched $C_{1-10}$-alkyl;
 c) halogen;
 d) hydroxy-$C_{1-10}$-alkyl;
 e) $C_{1-10}$-alkoxy;
 f) $C_{2-10}$-alkanoyloxy;
 g) $C_{2-10}$-alkene;
 h) $C_{2-10}$-alkene substituted with one or more groups selected from the group consisting of chlorine, fluorine, bromine or phenyl;
 i) $C_{1-10}$-alkoxycarbonyl;
 j) $C_{1-10}$-alkoxycarbamido;
 k) N-$C_{1-10}$-alkoxy-N-$C_{1-10}$-alkylaminocarbonyl;
 l) halo-$C_{1-10}$-alkyl;
 m) $C_{6-10}$-aryl;
 n) $C_{6-10}$-aryl substituted with one or more groups selected from the group consisting of ethyl, n-propyl, isopropyl, amino, methylamino and dimethylamino;
 o) —COOH or —COOY, wherein Y is a pharmaceutically acceptable cation;

$R_2$ is selected from the group consisting of
 1) —COOH;
 2) Cl or F;

3) trifluoromethyl;
4) —CHO; and,
5) —CH$_2$M, wherein M is selected from the group consisting of
   a) hydrogen;
   b) halo;
   c) hydroxy;
   d) C$_{1-10}$-alkoxy;
   e) C$_{6-10}$-aryloxy;
   f) C$_{6-10}$-aryl-C$_{1-10}$-alkoxy;
   g) mercapto;
   h) mercapto substituted with one or more groups selected from the group consisting of methyl, ethyl or phenyl;
   i) C$_{2-10}$-acylthio;
   j) C$_{2-10}$-acyloxy or carbamoyloxy;
   k) C$_{2-10}$-acyloxy or carbamoyloxy substituted with one or more groups selected from the group consisting of —COOH, aminophenyl, phenyl, C$_{1-6}$-alkyl, chlorine, bromine or fluorine;
   l) a quaternary ammonium salt;
   m) amino or amido group; and
   n) substituted amino or amido group;
R$_3$ is selected from the group consisting of
   a) hydrogen; and,
   b) pharmaceutically acceptable cations; and
an effective amount of a β-lactam antibiotic.

2. The method of claim 1 wherein the β-lactam antibiotic is amoxicillin or piperacillin.

3. A pharmaceutical composition, comprising: an effective amount of a compound of the formula (1)

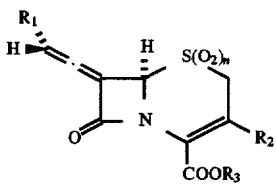

wherein n is 0 or 1;
R$_1$ is selected from the group consisting of
   a) hydrogen;
   b) linear or branched C$_{1-10}$-alkyl;
   c) halogen;
   d) hydroxy-C$_{1-10}$-alkyl;
   e) C$_{1-10}$-alkoxy;
   f) C$_{2-10}$-alkanoyloxy;
   g) C$_{2-10}$-alkene;
   h) C$_{2-10}$-alkene substituted with one or more groups selected from the group consisting of chlorine, fluorine, bromine or phenyl;
   i) C$_{1-10}$-alkoxycarbonyl;
   j) C$_{1-10}$-alkoxycarbamido;
   k) N-C$_{1-10}$-alkoxy-N-C$_{1-10}$-alkylaminocarbonyl;
   l) halo-C$_{1-10}$-alkyl;
   m) C$_{6-10}$-aryl;
   n) C$_{6-10}$-aryl substituted with one or more groups selected from the group consisting of ethyl, n-propyl, isopropyl, amino, methylamino and dimethylamino;
   o) —COOH or —COOY, wherein Y is a pharmaceutically acceptable cation;
R$_2$ is selected from the group consisting of
   1) —COOH;
   2) Cl or F;
   3) trifluoromethyl;
   4) —CHO; and,
   5) —CH$_2$M, wherein M is selected from the group consisting of
      a) hydrogen;
      b) halo;
      c) hydroxy;
      d) C$_{1-10}$-alkoxy;
      e) C$_{6-10}$-aryloxy;
      f) C$_{6-10}$-aryl-C$_{1-10}$-alkoxy;
      g) mercapto;
      h) mercapto substituted with one or more groups selected from the group consisting of methyl, ethyl or phenyl;
      i) C$_{2-10}$-acylthio;
      j) C$_{2-10}$-acyloxy or carbamoyloxy;
      k) C$_{2-10}$-acyloxy or carbamoyloxy substituted with one or more groups selected from the group consisting of —COOH, aminophenyl, phenyl, C$_{1-6}$-alkyl, chlorine, bromine or fluorine;
      l) a quaternary ammonium salt;
      m) amino or amido group; and
      n) substituted amino or amido group;
R$_3$ is selected from the group consisting of
   a) hydrogen; and,
   b) pharmaceutically acceptable cations; an effective amount of
   a β-lactam antibiotic; and
   a pharmaceutically acceptable carrier.

4. The composition according to claim 3, wherein the β-lactam antibiotic is amoxicillin or piperacillin.

* * * * *